United States Patent
Ellman et al.

(10) Patent No.: US 6,416,512 B1
(45) Date of Patent: Jul. 9, 2002

(54) ELECTROSURGICAL INSTRUMENT FOR EAR SURGERY

(75) Inventors: Alan G. Ellman; Jon C. Garito, both of Hewlett, NY (US)

(73) Assignee: Health Care Technologies, LLC., Hewlett, NY (US)

( * ) Notice: Subject to any disclaimer, the term of this patent is extended or adjusted under 35 U.S.C. 154(b) by 0 days.

(21) Appl. No.: 09/435,677

(22) Filed: Nov. 8, 1999

(51) Int. Cl.$^7$ ................................................ A61B 18/18
(52) U.S. Cl. .............................. 606/45; 606/41; 606/48
(58) Field of Search ............................... 606/39, 40, 41, 606/45, 46, 47, 48, 49, 50, 109; 607/98, 99, 115, 116, 137; 128/898

(56) References Cited

U.S. PATENT DOCUMENTS

| | | | |
|---|---|---|---|
| 5,403,311 A | * | 4/1995 | Abele et al. .................. 606/49 |
| 5,741,250 A | | 4/1998 | Garito et al. |
| 6,106,524 A | * | 8/2000 | Eggers et al. .................. 606/50 |
| 6,264,650 B1 | * | 7/2001 | Hovda et al. .................. 606/32 |

* cited by examiner

Primary Examiner—R. Kearney

(57) ABSTRACT

An electrode for use in an electrosurgical aural procedure known as a myringotomy for removing tissue of the tympanic membrane. In a preferred embodiment, the electrode is characterized by a bare active end portion having an outside diameter of 2 mm. In one embodiment, the bare end has a sharp circular edge; In another embodiment, the bare end has a tapered cone shape. When the electrode end is placed against the tympanic membrane and the electrosurgical apparatus activated, a 2 mm hole is punched in the tympanic membrane which allows any middle ear fluid to drain.

3 Claims, 3 Drawing Sheets

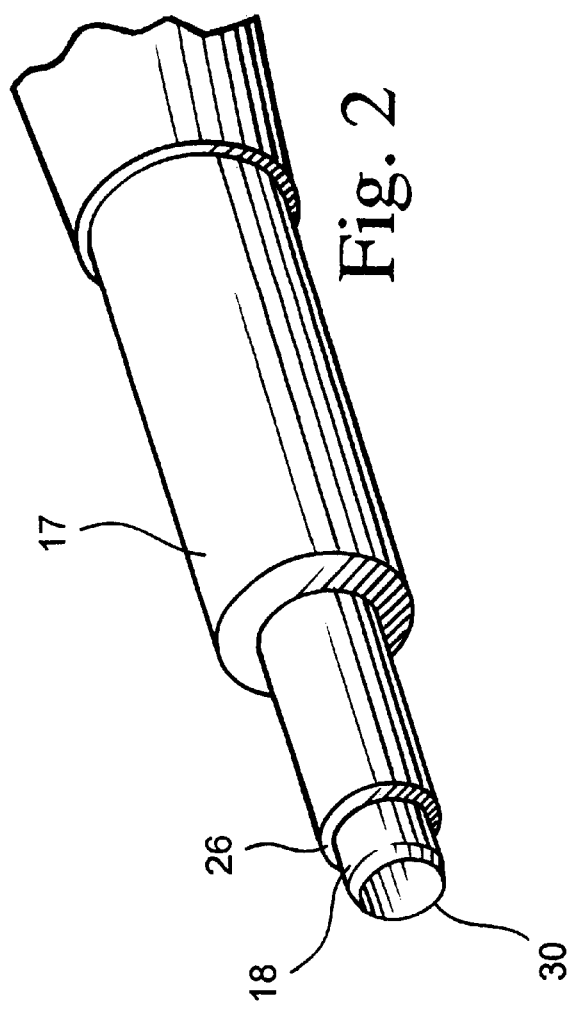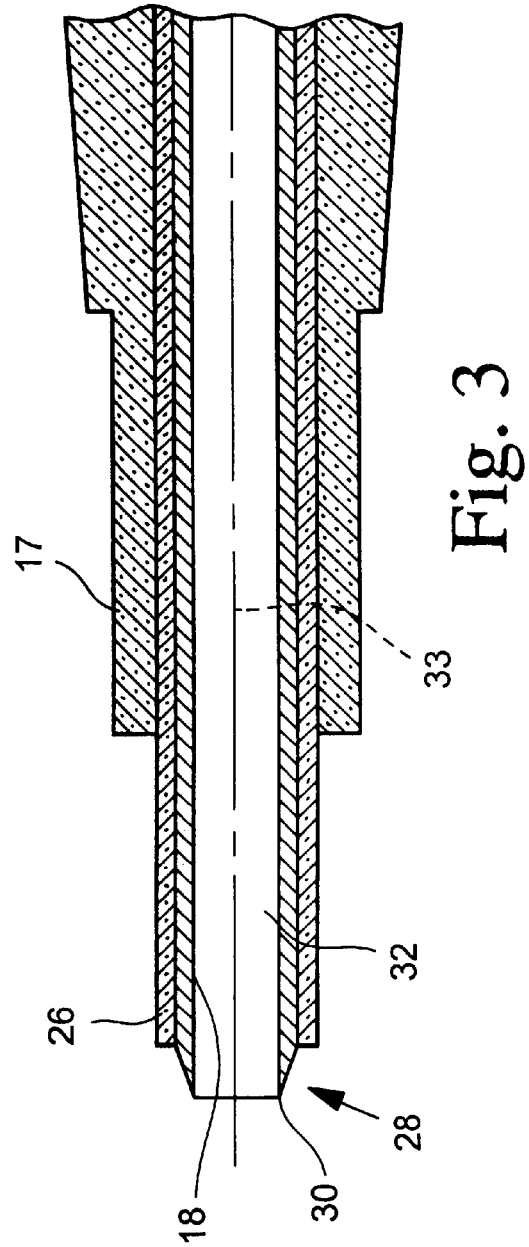

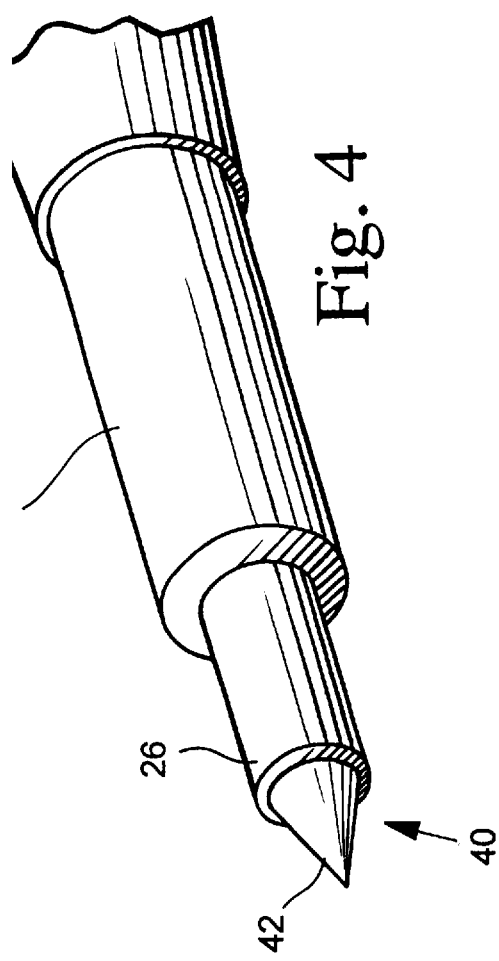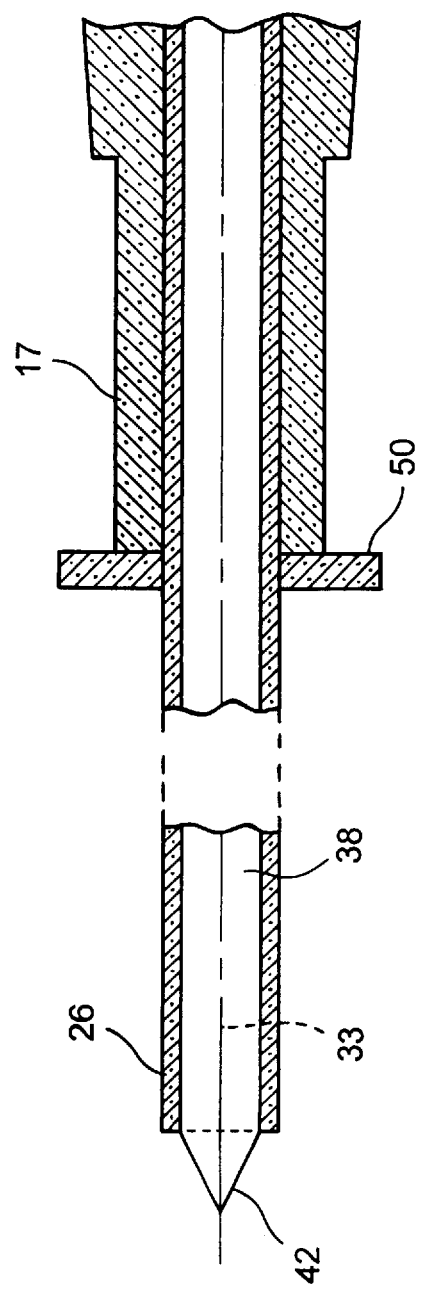

ELECTROSURGICAL INSTRUMENT FOR EAR SURGERY

This invention relates to an electrosurgical instrument for ear surgery, and in particular, for use in a myringotomy procedure.

BACKGROUND OF THE INVENTION

Reference is made to our prior issued U.S. Pat. No. 5,741,250, whose contents are incorporated herein by reference. This prior patent describes an improved myringotomy surgical procedure involving an incision of the tympanic membrane that is made to allow ventilation of the middle ear, to permit drainage of middle ear fluid, or to obtain cultures from an infected middle ear. The improved procedure uses a solid wire electrode and electrosurgical apparatus to form the hole in the tympanic membrane. The electrosurgical procedure has the important advantage of being able to cut the tissue while at the same time coagulating the cut tissue causing minimum bleeding. The structure of the novel electrode described in the prior patent used to make the incision prevents the excision depth from exceeding a safe value. In accordance with another feature of that invention, the electrode is uniquely configured to enable the active tip to reach the tympanic membrane via the ear canal passageway and incise the desired tissue while avoiding damage to surrounding tissue.

Recently, a new treatment called OtoScan Laser Assisted Myringotomy (OtoLAM) has been described. It uses a $CO_2$ laser to vaporize an allegedly precisely-sized preset hole in the tympanic membrane without damaging surrounding structures. The preset hole remains open for several weeks allowing ventilation of the middle ear and avoiding the need for grommets to keep the hole open until the middle ear region is adequately drained. The main disadvantage of this procedure is the use of a highly expensive laser instrument requiring training for those physicians that are not familiar with such equipment.

SUMMARY OF THE INVENTION

An object of the invention is an improved myringotomy surgical procedure.

We have invented a novel electrode for use in an electrosurgical myringotomy procedure. This electrosurgical procedure using our novel electrode enables physicians to offer to patients a treatment that is efficiently performed, easily learned and thus performed at a significantly reduced price, and with less tissue damage and bleeding compared to procedures done with a knife or needle.

The procedure using our novel electrode is based on forming the same kind of hole in the tympanic membrane as used heretofore, namely, an approximately 2 mm hole in the tympanic membrane, which is large enough to allow adequate drainage from the middle ear over several weeks, but not too large so as to delay healing. However, in accordance with a feature of our invention, electrosurgery is used to punch the hole in the tympanic membrane.

In a first preferred embodiment, a unipolar electrode is used with an electrode end that is hollow and is provided with a circular knife edge whose outer diameter is approximately 2 mm. In a second preferred embodiment, the electrode end is conically tapered from a solid end that has an outer diameter of approximately 2 mm. In both cases, the surgeon places the electrode end against the tympanic membrane and activates the electrosurgical apparatus. The result is to punch a hole in the membrane, by the flow of electrosurgical currents, that is of the same size as the outer diameter of the electrode end.

In comparison with the laser procedure, the electrosurgical equipment is far less expensive and many physicians are already trained in the use of electrosurgical apparatus. Moreover, for those untrained, the training procedure is relatively simple and consumes little time.

In accordance with another feature of the invention, the electrode end is configured with a stop to prevent the punch depth from exceeding a safe value. Preferably, the punch depth does not exceed more than about 70 mm. The latter restriction ensures that the entire depth of the tympanic membrane is penetrated but no further tissue damage will occur. As described in the prior patent, the electrode of the invention is also configured to enable the active tip to reach the tympanic membrane via the ear canal passageway and punch the desired tissue hole while avoiding damage to surrounding tissue.

In a preferred embodiment, our novel electrode is characterized by a straight electrically-insulating portion extending from an insulated handle and terminating in an active bare tip portion. The incision is effected with the bare tip moved by the surgeon in a generally straight path, and the adjacent portions of the tip support and electrode shaft are made insulating to prevent accidental burns to the patient and to allow the physician to use these insulated parts to help position and guide the active tip portion during the surgical procedure. The electrosurgical procedure has the important advantage of being able to punch the tissue while at the same time coagulating the cut tissue causing minimum bleeding. It is preferred that the electrosurgical currents used be above 2 MHz, and preferably above 3 MHz. At these high frequencies, commonly referred to as radiosurgery, cutting is accomplished by volatilizing intracellular fluids at the point of the transmitting electrode contact which is primarily responsible for only small lateral heat spread and thus less damage to neighboring cell layers.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention, like reference numerals or letters signifying the same or similar components.

BRIEF DESCRIPTION OF THE DRAWINGS

In the drawings:

FIG. 2 is a perspective view of the working end of the electrode of FIG. 1;

FIG. 3 is a cross-sectional view of the working end of the electrode of FIG. 1;

FIG. 4 is a perspective view of a second embodiment of an electrosurgical myringotomy punch electrode in accordance with the invention;

FIG. 5 is a cross-sectional view of the working end of a third embodiment of an electrosurgical myringotomy punch electrode in accordance with the invention.

DETAILED DESCRIPTION OF THE PREFERRED EMBODIMENTS

Figure 1:
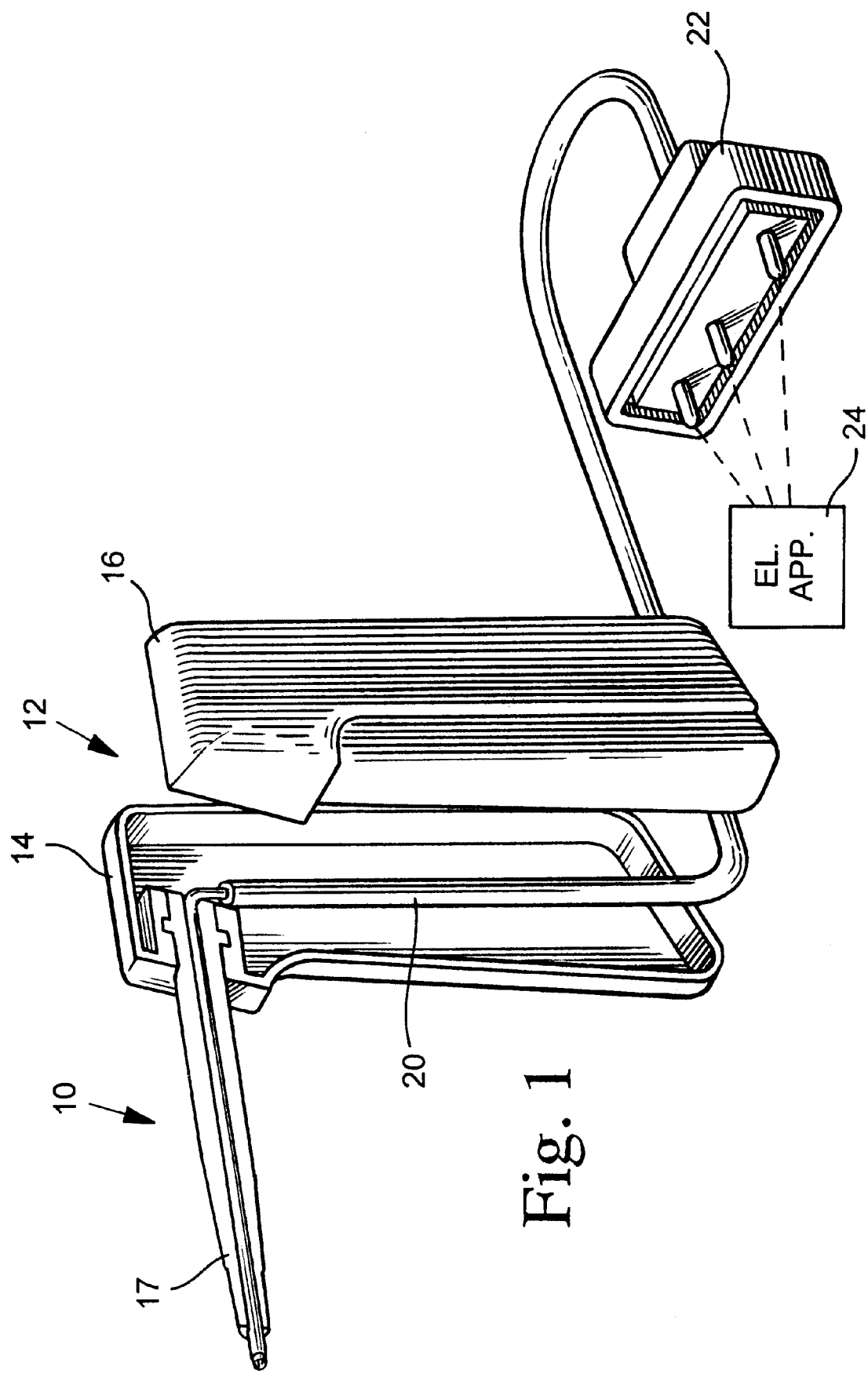
FIG. 1 is a perspective, partly exploded view of a first embodiment of an electrosurgical myringotomy punch electrode in accordance with the invention, shown connected to electrosurgical apparatus.

FIG. 1 illustrates a first preferred form of the unipolar electrosurgical myringotomy punch electrode 10 of the invention. It comprises a handle 12 of electrically-insulating material made up of two separable parts 14, 16 that allows separation of the handle to permit insertion of another form of myringotomy punch electrode. The form of myringotomy punch electrode shown in FIG. 1 comprises a straight elongated insulating tube 17 enclosing an elongated electrically-conductive tube 18, for example of metal, extending throughout its length and connected at its inner end to a cable 20 which is connected via a conventional plug 22 to conventional electrosurgical apparatus 24. As an example only, the electrosurgical apparatus can be model Dual Frequency Surgitron available from Ellman International, Inc. of Hewlett, N.Y. The Ellman equipment is preferred due to its high operating frequency, typically above 2 MHz, preferably at 3.8–4.0 MHz.

The portion of the rod 18 projecting from the end of the electrically-insulating tube 17 is coated with a thin electrically-insulating coating 26, except for a short bare part 28 terminating in a circular sharp edge 30 surrounding a center bore 32 having a longitudinal axis 33. The sharp edge 30 which is bare and lies in a common plane (vertical in FIG. 3 of the drawing) perpendicular to the longitudinal axis 33 serves as the working end of the electrode. Also connected to the electrosurgical apparatus 24 is the usual indifferent plate (not shown) which during use is in contact with a patient's body. When the electrosurgical apparatus 24 is energized, high frequency electrosurgical currents are generated which are coupled by way of the cable 20 and electrically-conductive tube 18 to the active, bare end 28. The physician, in the usual way, holds the handle 12 while applying the active working end 28 of the unipolar electrode to the desired area of the patient to be treated.

In accordance with a feature of the invention, the diameter of the circular sharp edge is 2 mm. When the 2 mm sharp edge is placed against a patient's tympanic membrane and the electrosurgical apparatus activated, a 2 mm hole is punched by the electrosurgical currents in the tympanic membrane. The surgeon may find it necessary to advance the electrode 10 about 70 mm, which is the typical thickness of the tympanic membrane, to ensure that the hole has completely penetrated the membrane. Nothing more needs to be done. No incision is required. The hole punched by electrosurgical currents from the electrode 28 is of the approximately 2 mm size required for adequate drainage of the inner ear cavity without requiring grommets to keep the hole open yet without delaying the healing time.

The electrically-insulating coating 26 together with the electrically-insulating tube 17 ensures that the only active part of the electrode is the short bare portion 28 in front thereby preventing inadvertant burns or other damage to other ear parts.

FIG. 4 shows a second embodiment. The handle construction can be the same. The only difference is that a solid center rod 38, for example, of metal, ends in a bare end 40 of the electrode that now terminates in a tapered cone 42. The electrode or rod OD remains the same at 2 mm. The taper defines a cone angle that can vary between about 35° and 90°. The operation is the same as before. The surgeon places the tapered cone end 42 of the electrode against the tympanic membrane and activates the electrosurgical apparatus, and advances the electrode into the ear cavity until the hole formed by the electrosurgical currents penetrates through the tympanic membrane. The handle 12 can be opened and the electrode of FIG. 4 mounted within the handle to replace that of FIG. 1.

The variation of FIG. 5 is to extend the electrically-insulated working end sufficient to provide an enlarged shoulder 50 positioned about 70 mm from the cone end of the electrode. The shoulder 50, which may be of electrically-insulating material, can serve as a stop to ensure that the surgeon does not advance the electrode more than about 70 mm which can cause damage to the inner ear region.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. A myringotomy surgical procedure for a patient, comprising the steps:

(a) providing electrosurgical apparatus connected to a handle holding an electrosurgical electrode, said electrosurgical electrode comprising:

(i) an electrically-conductive shaft member having a first end mounted to the handle and a second end, (ii) said second end having an active, electrically-conductive, end portion, (iii) said active end portion being exposed electrically for applying high-frequency electrosurgical currents to said tympanic membrane when said shaft member is connected to a source of electrosurgical currents, (iv) the portions of said shaft member adjacent said exposed end portion being electrically-insulating to prevent contact and passage of electrosurgical currents to tissue areas adjacent to or surrounding the hole to be punched, (v) said active end portion comprising a hollow tube terminating in a circular sharpened edge having a diameter of about 2 mm the circular sharpened edge lying in a common place extending perpendicular to the longitudinal axis of the active end portion, (b) inserting the electrode into the ear canal until the active end portion reaches the tympanic membrane tissue of the patient and activating the electrosurgical apparatus punching a 2 mm hole through the tympanic membrane, (c) withdrawing the electrode after the 2 mm hole has been punched.

2. A myringotomy surgical procedure for a patient as claimed in claim 1, further comprising means forming a stop where said active end portion meets the adjacent portions of said shaft member, said stop being sufficiently wide to prevent tissue penetration of said active end portion beyond a length of approximately 70 mm.

3. The procedure of claim 2, wherein the high frequency currents are at a frequency exceeding 3 MHz.

* * * * *